United States Patent [19]
Abel

[11] Patent Number: 5,280,780
[45] Date of Patent: Jan. 25, 1994

[54] OXYGEN DELIVERY AND CONSERVING DEVICE

[76] Inventor: Elaine R. Abel, P.O. Box 91538, Henderson, Nev. 89009

[21] Appl. No.: 973,674

[22] Filed: Nov. 9, 1992

[51] Int. Cl.$^5$ .............................................. A61M 16/00
[52] U.S. Cl. ........................... 128/203.14; 128/200.24; 128/205.24; 128/207.14; 128/203.12; 128/207.18
[58] Field of Search .............. 128/200.24, 203.12, 128/203.25, 203.14, 203.28, 204.18, 204.26, 205.24, 207.14, 207.18

[56] References Cited

U.S. PATENT DOCUMENTS

| | | | |
|---|---|---|---|
| 3,005,453 | 10/1961 | Wellenstein | 128/203.14 |
| 3,513,843 | 5/1970 | Exler | 128/203.25 |
| 3,788,310 | 1/1974 | Fleischmann | 128/203.14 |
| 3,848,605 | 11/1974 | Harautuneian | 128/207.14 |
| 4,535,767 | 8/1985 | Tiep et al. | 128/207.18 |
| 4,572,177 | 2/1986 | Tiep | 128/205.17 |
| 5,056,515 | 10/1991 | Abel | 128/207.15 |

FOREIGN PATENT DOCUMENTS

| | | | |
|---|---|---|---|
| 8900818 | 11/1990 | Netherlands | 128/200.24 |
| 20911 | of 1911 | United Kingdom | 128/203.25 |

OTHER PUBLICATIONS

Direction Sheet for Oxymizer Pendant TM—manufactured for Chad Therapeutics, Inc. 9445 De Soto Ave., Chatsworth, Calif. 91311, printed May 1989.

Primary Examiner—David A. Wiecking
Assistant Examiner—Eric P. Raciti

[57] ABSTRACT

An apparatus for conserving oxygen delivered to a patient including a flat annular housing with an interior chamber having an outlet and inlet port, with the outlet port affixed to a flow check valve. The interior chamber is divided by a flexible diaphragm with the diaphragm and one wall of the housing defining an oxygen storage reservoir which communicates with the outlet and inlet ports. The inlet port directs oxygen from an oxygen tank into the reservoir, and the outlet port directs oxygen through the check valve to the patient. During inhalation, the patient inhales oxygen from the storage chamber through the check valve, thus collapsing the diaphragm. During exhalation the check valve closes, preventing introduction of potentially infectious exhaled air into the system and allowing oxygen to accumulate within the oxygen storage chamber instead of being wasted and expelled during exhalation.

2 Claims, 3 Drawing Sheets

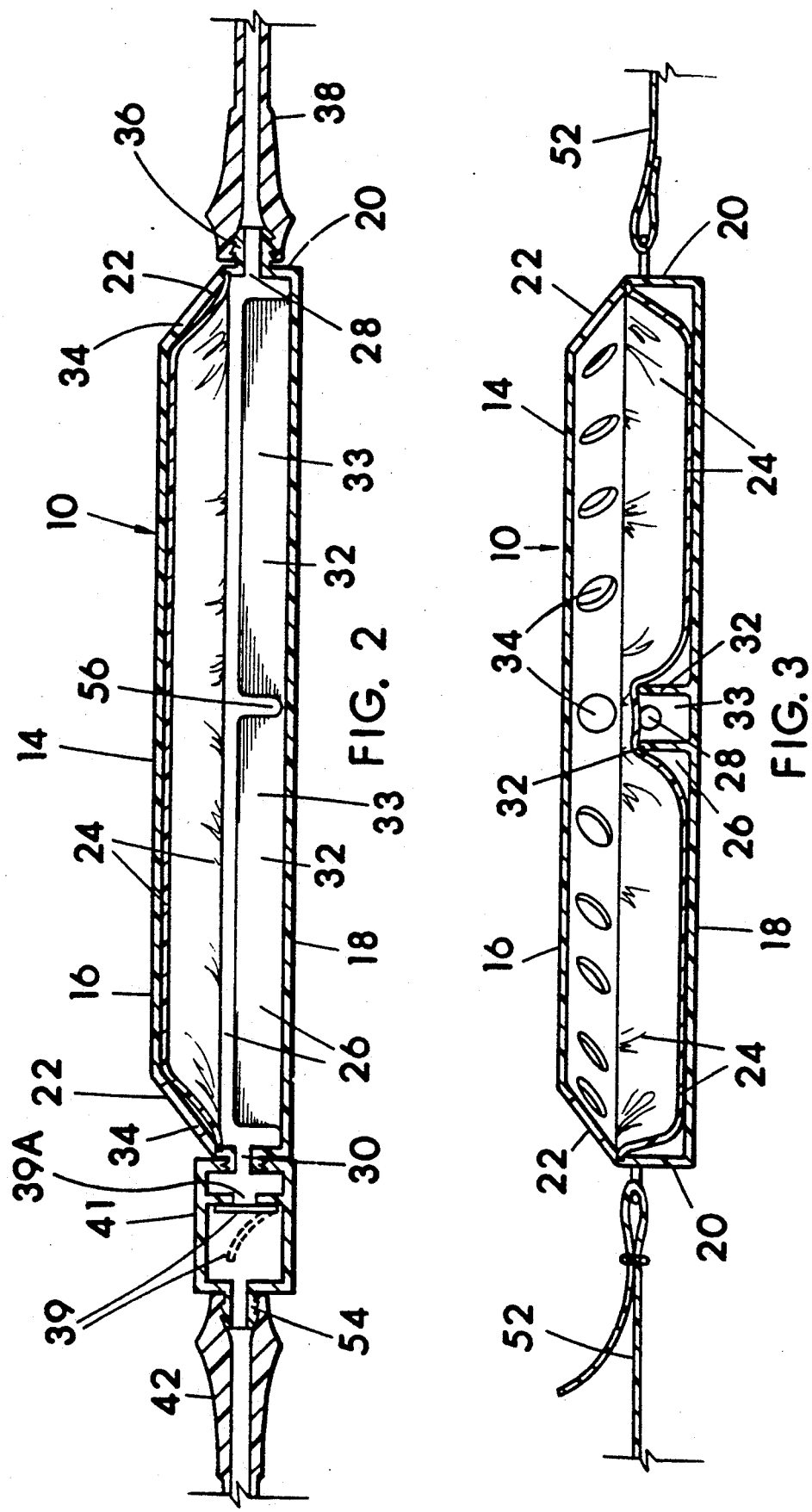

OXYGEN DELIVERY AND CONSERVING DEVICE

BACKGROUND OF THE INVENTION

1. Field of the Invention:

This invention relates to devices for conserving oxygen as utilized in supplemental oxygen therapy for human patients, particularly those receiving oxygen therapy via a tracheostomy tube assembly.

2. Description of the Prior Art:

Long term conventional oxygen therapy is commonly prescribed for patients who have compromised respiratory capabilities, often resulting from an acute infection or a chronic illness, such as emphysema. While these patients are capable of normal or nearly normal respirations, their oxygen exchange is not sufficient and it must be supplemented. Some pulmonary conditions have also required the use of a tracheostomy tube with oxygen supplied directly to the patient's trachea. The majority of the patients receiving supplemental oxygen, either through a nasal cannula or tracheostomy tube, utilize conventional oxygen therapy equipment which includes a pressurized oxygen tank with a regulator and an oxygen line endwardly connected to the nasal cannula, or tracheostomy tube. Sometimes a humidifying unit is also used with oxygen therapy equipment. These patients still breath the ambient air but are merely supplemented with additional oxygen. For patients having a chronic pulmonary problem, they must receive supplemental oxygen on a long term or permanent basis. There have been several disadvantages noted with the conventional long term management of oxygen therapy patients. Since the oxygen is supplied at a continuous flow rate, the patient is still administered oxygen during exhalation as well as inhalation. During exhalation, the oxygen supplied by the oxygen tank is expelled with the patient's exhaled air, thus wasting the oxygen. Therefore, more oxygen is dispensed from the oxygen tank than is actually used by the patient. This is not only a waste of money but refills of portable oxygen tanks are made much more often than would otherwise be necessary. Since oxygen is dispensed constantly, the nasal mucosa and other tissues of the patient can become dehydrated, and humidification of the oxygen is therefore sometimes necessary, which is also another added expense.

Another disadvantage of the traditional oxygen therapy equipment is the air exhaled by the patient must exceed the pressure of the dispensed oxygen through the tracheostomy tube in order to be expelled through the nose or mouth around the cannula, thus requiring the patient to exhale slightly more forcefully than normal to exhale against this pressure. For weak and debilitated patients this can actually be tiring over an extended period of time.

Conventional oxygen therapy equipment also does not compensate for the temperature of the dispensed oxygen, which at times can be disagreeably cold to the patient. If the temperature were consistently cold and administered over an extended period of time, the patient's temperature could conceivable be lowered, possibly compromising the patient's health, not to mention the patient's comfort.

There are several past art devices which function as oxygen conserving devices. One such device is the oxygen delivery apparatus patented by Tiep et al, U.S. Pat. No. 4,535,757. Tiep's device is available as an accessory attachment to existing oxygen equipment, and functions to conserve oxygen by temporarily restricting the flow of oxygen out the nasal cannula during exhalation, utilizing the pressure differentials between the oxygen flow and the patient's exhalations. This is accomplished by providing a narrow elongated chamber with a flexible diaphragm, wherein the diaphragm blocks the outlet ports of the nasal cannula during the last phase of inhalation. During exhalation, the patient's exhaled air fills the chamber and forces the diaphragm aside, allowing oxygen to mix with the exhaled air. Thus the flow of oxygen is temporarily directed into the chamber when the patient exhales instead of being dispensed out the nasal cannula, thus saving oxygen.

There are several disadvantages to the Tiep et al device, one being the fact that the patient is rebreathing his own exhalations and therefore the oxygen which is administered to the patient is diluted. By diluting the oxygen mixture which the patient is prescribed, he may not be receiving sufficient oxygen to be beneficial or therapeutic. The chamber of the Tiep device is also relatively small and retains a fixed volume of oxygen, which may be sufficient for sedentary patients. However, this fixed volume would not be of sufficient volume to compensate the patient during exertion when the demand for oxygen would be greater. Even during sedentary states, all people need to occasionally take in a large cleansing breath, which the Tiep device would not compensate for.

Another more significant disadvantage of the Tiep et al device in that the exhaled air forced into the chamber could carry potentially infectious germs which could accumulate within the chamber and create a source for respiratory infections. The patient's exhalations are warm and moist and help to create a favorable environment within the chamber for growing the microbes. Also, the moisture of the exhalations could condense and accumulate, causing blockage problems. Many patients on oxygen therapy are generally already in a medically compromised condition or they wouldn't be needing the supplemental oxygen, and respiratory infections are especially serious to these patients since it is their lungs which are generally debilitated. Infections which would be minor to healthy individuals can be potentially lethal to patients with pulmonary deficiencies.

Another oxygen conserving device, currently in the market place, is sold under the tradename of OXYMIZER PENDANT, marketed by Chad Therapeutic, Inc., 9445 De Soto Ave, Chatsworth, Calif. 91311. The OXYMIZER PENDANT includes a bladder or diaphragm housed within an annular housing which is connectable between the oxygen tank and a nasal cannula. The OXYMIZER PENDANT saves oxygen by creating pressure differentials between the force of the patient's exhalation and the dispensed oxygen. Pressure increases in the nasal cannula, tubing and bladder as the patient exhales, forcing the lower pressurized oxygen dispensed from the tank to back-up within the bladder instead of being expelled upon exhalation, and thus wasted. The disadvantage of this system also involves the dilution of the oxygen with the exhaled used air. This is most significant when the patient is under stress or physical exertion where the force of exhalation is much greater than during sedentary periods. During exertion, much more exhaled air is forced into the air lines and possibly into the bladder or reservoir, significantly reducing the overall amount of oxygen available to the patient. Since the patient would require much more oxygen during exertion, the reduction in oxygen due to the dilution factor could adversely affect the patient. Therefore, the pressure differentials under which the OXYMIZER PENDANT best functions, only exist within a narrow range of parameters with the patient presumably remaining sedentary and the pressure of the oxygen dispensed from the tank remaining lower than the pressure of the patient's exhalations. Any variations in these parameters and a significant amount of oxygen can be lost, thus reducing the savings.

More importantly, the OXYMIZER PENDANT also allows the introduction of exhaled air into the air line and possibly even into the storage bladder. The exhaled air, as previously mentioned, can carry microbes which could lead to infection, and could even cause chronic or recurrent respiratory problems for the patient. Moisture condensation from the exhalations could also prove a problem by accumulating and causing partial or complete blockage of the oxygen flow.

Additionally, the OXYMIZER PENDANT apparently has no structural arrangement which would allow it to be used for introducing oxygen into a tracheostomy tube or assembly, which is becoming an increasingly popular method of applying oxygen therapy.

There is therefore a need for an oxygen conserving device which prevents the potential introduction of infectious agents into the oxygen system and provides the patient with oxygen undiluted with carbon dioxide, and which can also be utilized with tracheostomy tube assemblies.

SUMMARY OF THE INVENTION

The present invention includes an oxygen conservation device which is provided as an accessory attachment to existing oxygen therapy equipment. My oxygen conserving device reduces the amount of wasted oxygen during oxygen therapy. My oxygen conserving device preferably includes a flat annular housing having an open interior chamber divided by a flexible diaphragm, with the oxygen directed through the housing and out through a one-way flow-directing check valve where it is finally administered to the patient. The oxygen conserving device is connectable along the existing oxygen line between the oxygen source and a tracheostomy tube assembly such as is taught in my previous U.S. Pat. No. 5,056,515, issued Oct. 15, 1991, titled Tracheostomy Tube Assembly, which is herein incorporated by reference as part of this disclosure. My oxygen conserving device can also be connected to a nasal canula if desired. A tracheostomy tube assembly generally consists of a curved tube inserted into an opening in the patient's trachea which keeps the opening patent and allows for connection of equipment such as a respirator or oxygen line. It should be noted that the tracheostomy patient, as well as the patient using a nasal cannula, is not absorbing only pure oxygen during oxygen therapy since the patient still possesses respiration capabilities wherein ambient air is still inhaled and exhaled through the mouth and nose.

The oxygen reservoir of the present invention includes a narrow annular housing having an internal diaphragm which defines an expandable and collapsible storage chamber into which oxygen is directed from the oxygen tank or other source of oxygen. The check valve, located between the tracheostomy tube assembly and the reservoir, prevents the back flow of exhaled air from the tracheostomy tube assembly into the oxygen tubing and the reservoir. As the patient exhales, positive pressure is created within the oxygen tubing between the tracheostomy tube assembly and the check valve. The positive pressure of exhalation is exerted against the check valve, closing it. The check valve is slightly biased to be normally closed, and the positive pressure of exhalation functions to assist the check valve in overcoming positive pressure in the reservoir allowing the check valve to fully close. Since the oxygen tubing between the tracheostomy tube assembly and the check valve already contains oxygen, the back pressure is in effect instantaneous and no exhaled air enters the connecting tubing. The oxygen dispensed from the tank, being blocked at the closed check valve, then begins to fill the reservoir with the now collapsed diaphragm. The collapsed diaphragm ensures space for the in-flowing oxygen to enter the reservoir without being opposed by positive pressure. As the oxygen enters the reservoir, the highly flexible diaphragm moves outward into what I call an expanded position. Upon inhalation by the patient, the check valve opens, partially due to the negative pressure caused by inhalation between the tracheostomy tube assembly and the check valve, and also due to the increased positive pressure behind the check valve within the reservoir which has been filled with oxygen. The oxygen contained within the reservoir is drawn up into the oxygen tubing, collapsing the diaphragm as the oxygen is withdrawn, and exits through the tracheostomy airline attachment directly into the patient's trachea. Although the diaphragm is collapsed at that stage, there are ridges on the interior floor of the housing which support the central section of the diaphragm forming an open passageway which allows oxygen to continuously pass through the reservoir during inhalation. Therefore the flow of oxygen is not blocked in the reservoir even when the diaphragm is collapsed, provided inhalation is still occurring to a sufficient degree. The check valve, therefore, operates in direct response to the patient's respirations, with the patient receiving oxygen during the entire extent of his or her inhalation. This is significant even for sedentary patients since it is necessary for people to always occasionally sigh or take in a deep cleansing breath, and regardless of the length of the inhalation, oxygen is constantly provided. The present invention is particulary useful during exertion by the patient since it provides oxygen on demand with the check valve closing only during exhalation. Since these patients are in generally guarded health to begin with, even light ambulation can stress them to the point where they are winded and definitely require the total volume of oxygen they are prescribed, without it being diluted. Some patients are also improving in health to the point that they can start exercise programs to increase their strength. The added exertion of the exercise places a greater demand on their lungs and therefore more oxygen is preferable at those times.

The volume of oxygen originally prescribed by the doctor for the patient can be reduced twenty-five to fifty percent when using this device, since some of the oxygen is not wasted during exhalation. The savings depends on several factors including the patient's respiration rate, and the pressure of the dispensed oxygen. The higher pressure dispensed oxygen may necessitate a slightly stronger biasing of the check valve toward the closed position, although the majority of patients have oxygen prescriptions which function adequately well with a moderately set biasing strength in the check valve.

The reservoir housing is manufactured of a soft semi-resilient plastic and is generally flat and annular in shape. The air lines exit the housing from the curved sides thereby allowing the device to lie flat against the patients chest with one line exiting the top of the reservoir and one exiting the bottom. The flat shape of the housing also helps to better conceal the device beneath the patient's clothing, which helps the patients feel less self conscious about their condition or disability. Wearing the device beneath the clothing also helps to prevent it from getting in the patient's way or becoming caught on something. The oxygen tubing can enter under the patients shirt at the waist and be concealed along with the reservoir underneath the clothing. This invention is therefore ideally suited for ambulatory patients having portable oxygen tanks.

One embodiment of the invention is provided with an adjustable strap for attachment around the chest area to be worn beneath clothing. The attachment strap also functions to reduce pull on the tracheostomy tube from the weight of the device, which although it is light even slight pressure applied against the tracheotomy may become uncomfortable over an extended period of time. Another embodiment contains two reservoirs which are structured to fit within the brassiere of a female patient, thus allowing the elimination of the attachment strap, with the brassiere providing the support for the device.

The thin flat structure of the reservoir also provides more surface area with which to absorb body heat from the patient, thereby warming the oxygen prior to being utilized by the patient. Dispensing oxygen which is very cold could conceivably lower the patient's body temperature which may result in a health problem, and the cold temperature of the oxygen could also have a tendency to be irritating or uncomfortable to the lining of the patient's trachea.

A major object of this invention is to save oxygen which is cost effective to the patient and also allows longer intervals between refills of portable tanks. This enables ambulatory patients to be away for longer periods of time. The amount of the oxygen savings is relative to the strength and duration of the patient's exhalations, with the check valve remaining closed for longer periods with longer exhalations. However, to avoid the reservoir from expanding too much and exploding, the check valve is overridden when pressure in the reservoir reaches a predetermined setting.

Since there is not a constant flow of oxygen when utilizing this device as compared to a conventional oxygen therapy system, there is less of a drying effect on the tracheal tissues and humidification is not generally required, which is another cost effective factor.

The present invention therefore overcomes the previously mentioned disadvantages associated with conventional oxygen therapy and the past art oxygen conserving devices. This invention also provides new and useful improvements not provided in the past art.

BRIEF DESCRIPTION OF THE DRAWINGS

FIG. 2 is a cross section of the housing and affixed check valve of FIG. 1 through both inlet and outlet ports, showing the diaphragm in the inflated stage. The check valve is shown closed due to the back pressure of the patient's exhalation.

FIG. 3 is a cross section of the housing in FIG. 1 through the strap, depicting the two ridges and showing the diaphragm in the collapsed stage.

DESCRIPTION OF THE PREFERRED EMBODIMENTS

Figure 1:
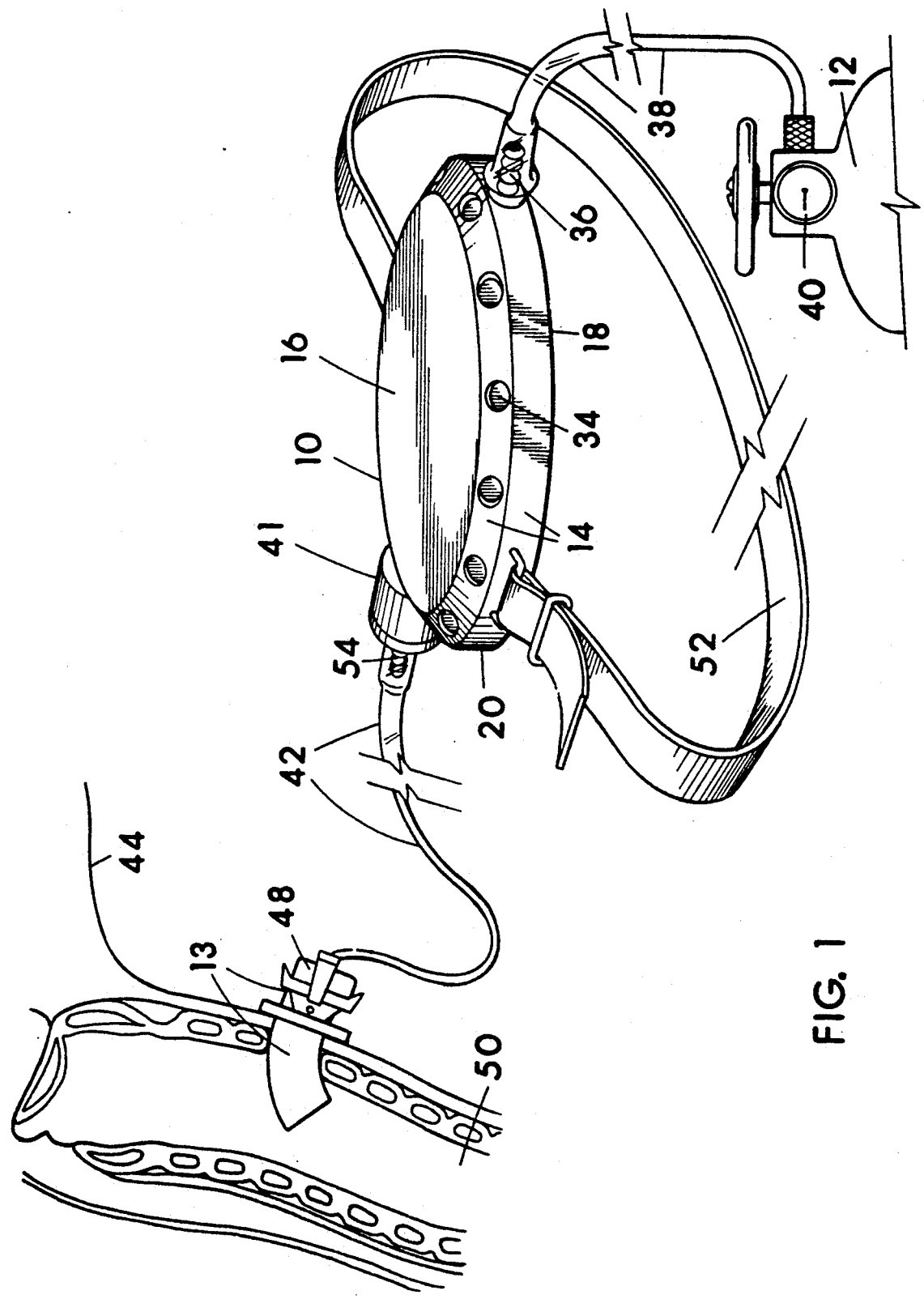
FIG. 1 is a top perspective view of a preferred embodiment of the invention showing the housing and affixed check valve connected to an oxygen tank on one end and to a tracheostomy tube on the other. An attachment strap is also shown affixed to the housing for connection around the chest or waist of the patient.

Referring now to FIG. 1 where a preferred embodiment 10 of the present invention is shown attached to oxygen tank 12, and to tracheostomy tube 13. Embodiment 10 of the present invention includes a small lightweight flexible flat annular housing 14 formed of two mating sections; top housing section 16 and bottom housing section 18. Housing 14 is preferably manufactured of a lightweight semi-rigid plastic material. Top housing section 16 and bottom housing section 18 are affixed along a circumferential vertical side wall 20 with top housing section 16 having an outer beveled edge 22. Both top and bottom housing sections 16 and 18 collectively form an open interior chamber which is longitudinally divided by diaphragm 24. Diaphragm 24 is a flat circular section of non-porous flexible material, preferably plastic, which is edgewardly affixed to housing 14 along the attachment seam of both housing sections 16 and 18. Diaphragm 24 and the interior section of bottom housing section 18 define an interior opening or reservoir 26. The volume of oxygen retained in reservoir 26 is dependant upon the size of housing 14, with reservoir 26 retaining anywhere between 25 and 100 ml of oxygen. Two openings in side wall 20 of bottom housing section 18 open into reservoir 26. One opening is referred to as inlet port 28 and the other oppositely disposed opening is referred to as outlet port 30. The interior floor of bottom housing section 18, within reservoir 26, contains two central parallel ridges 32. The open ends of ridges 32 are positioned adjacent ports 28 and 30, but do not connect to side wall 20. There is also a central notch 56 formed in each ridge 32, best shown in FIG. 2. Ridges 32 support the central section of diaphragm 24 forming an open passageway 33 between inlet port 28 and outlet port 30 when diaphragm 24 is deflated. The beveled edge 22 of top housing section 16 contains a series of vents 34 which allow circulation of ambient air into the interior of housing 14, which prevents the creation of a vacuum between diaphragm 24 and top housing section 16. By placing vents 34 through beveled edge 22, there is less chance of vents 34 becoming obstructed when housing 14 is positioned against a flat surface or worn against the body. Inlet port 28 is affixed with a short tubular stem 36 for releasable connection to air line 38. Air line 38 directs oxygen dispensed from an oxygen source, such as a portable oxygen tank 12, to reservoir 26. The volume of oxygen dispensed from oxygen tank 12 is controlled by a conventional regulator 40, With the specific volume of oxygen, requiring a doctor's prescription.

Outlet port 30 is directly affixed to check valve 41 which is a conventional one-way fluid valve allowing flow of oxygen from reservoir 26 to oxygen tubing 42 only. Although several types of check valves are suitable, for this disclosure check valve 41 includes a housing having an entrance and exit port, with the housing containing a small flexible annular flap or gate 39 which releasably seals an opening 39A which in turn effectively shuts off the flow of oxygen through the housing. Oxygen tubing 42 conveys the oxygen from reservoir 26, through opening 39A of check valve 41, to patient 44 via tracheostomy tube 13. Tracheostomy attachment 48 is required for connection of oxygen tubing 42 to tracheostomy tube 13, and includes a small annular plug which prevents passage of ambient air, allowing only passage of oxygen into the trachea 50 of patient 44. Patient 44 still breaths in ambient air through the nose and mouth while the oxygen is dispensed through the tracheostomy attachment 48.

Embodiment 10 of the present invention is affixed with an adjustable strap 52 which is connected at each end to side wall 20 of housing 14, with each end oppositely disposed to one another, transverse to ports 28 and 30. At least one end of strap 52 is adjustably affixed to housing 14 and allows for length adjustments to compensate for variations in the size of patients 44. With strap 52, housing 14 can be affixed around the chest or waist of patient 44 underneath the clothing. Strap 52 secures housing 14 in place and prevents the weight of the device from pulling directly on tracheostomy tube 13 through oxygen tubing 42, which could be quite uncomfortable to the stoma or tracheal opening of patient 44.

To connect embodiment 10 onto existing oxygen therapy equipment, the nasal cannula must first be removed from the end of air line 38, since the majority of existing oxygen therapy equipment will already have a nasal cannula. The female connector on the end of air line 38 is designed for easy frictional attachment to the nasal cannula, and can be removed by pulling the attachment apart. The short stem 36 affixed to inlet port 28 of housing 14 contains small beveled ridges which help to maintain frictional attachment of air line 38 to housing 14. The end of check valve 41 is also affixed with a stem 54 which allows for attachment of oxygen tubing 42. Oxygen tubing 42, along with tracheostomy attachment 48 will preferably be provided along with embodiment 10 as a unit. Tracheostomy attachment 48, already permanently affixed endwardly to oxygen tubing 42, is adapted for snap-on attachment to the exterior of the opening of tracheostomy tube 13.

Oxygen is then dispensed from oxygen tank 12 and regulated, as per the physician's order, at regulator 40. The physician can, however, now reduce the amount of oxygen normally prescribed by 25% to 50% when using the present invention. The oxygen is dispensed under a mild yet constant pressure through air line 38 to inlet port 28 and into reservoir 26. As patient 44 inhales, the oxygen which has accumulated within reservoir 26 is drawn up through outlet port 30, through the open check valve 41, and through oxygen tubing 42 to tracheostomy tube 13 and to the trachea 50 of patient 44. Check valve 41 is normally closed, but the pressure of the oxygen within reservoir 26 forces check valve 41 to be open most of the time. During exhalation, the air exhaled by patient 44 is forced against the end of oxygen tubing 42 which already contains oxygen, and creates a back pressure against gate 39 which forces gate 39 against aperture 39A in check valve 41 to close aperture 39A. In FIG. 2 gate 39 in solid lines is shown closing aperture 39A, and in dotted lines gate 39 as it would be when aperture 39A is open. Since there is already oxygen contained within oxygen tubing 42, the exhaled air is not forced down into oxygen tubing 42 and therefore does not dilute or displace the oxygen. While check valve 41 is closed, oxygen is still being dispensed from oxygen tank 12 and as it builds up, follows the path of least resistance which is into reservoir 26. When patient 44 inhales, the oxygen within oxygen tubing 42 is withdrawn, creating a slight vacuum or negative pressure, releasing the pressure off of check valve 41 and allowing the withdrawal of the oxygen within reservoir 26. This causes diaphragm 24 to deflate and collapse over ridges 32. If inhalation is prolonged or intensive and all the reserved oxygen is withdrawn from reservoir 26 before the end of the inhalation, the oxygen can still flow through reservoir 26, under the deflated diaphragm 24, through passageway 33. Notches 56 are incorporated into the central section of each ridge 32 to further assist the removal of the oxygen from reservoir 26. This allows patient 44 access to the maximum amount of oxygen during periods of exertion when it is most needed. The most significant advantage of this invention however, it that the introduction of potentially infectious microbes are prevented from entering the device due to check valve 41.

Figure 4:
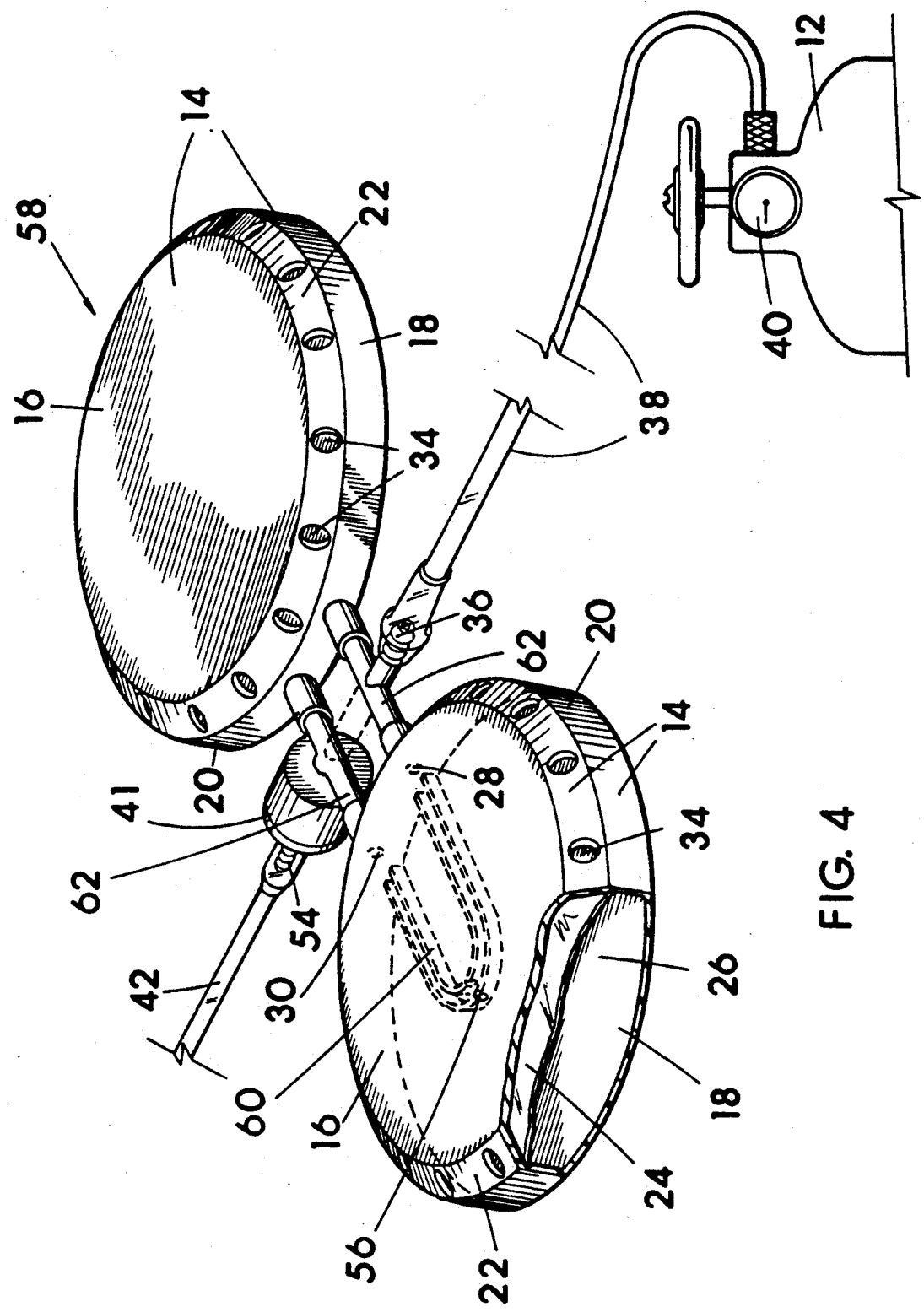
FIG. 4 is a top perspective view of another embodiment of the invention showing double reservoirs.

Another preferred embodiment 58 of the invention is illustrated in FIG. 4 and includes the use of two reservoirs 26. Embodiment 58 includes two housings 14 of similar construction to that of embodiment 10, with the exception of internal ridges 32. Embodiment 58 contains two parallel U-shaped ridges 60 having the distal open ends positioned adjacent inlet port 28 and outlet port 30, which are positioned next to one another on side wall 20. Notches 56 are also included the U-shaped ridges 60 of embodiment 58. Both housings 14 of embodiment 58 are affixed to one another with two parallel connecting tubes 62. The first connecting tube 62 is centrally affixed with stem 36 for attachment to air line 38, and endwardly affixed to each inlet port 28 of both housings 14. The second connecting tube 62 is centrally affixed directly to check valve 41, with the terminal ends affixed to outlet ports 30 of both housings 14. Embodiment 58 functions the same as embodiment 10 but provides a larger reservoir 26 for storage of more oxygen. Although two connecting tubes 62 are preferred for rotational stability of housings 14, and for quicker evacuation of reservoirs 26, one connecting tube 62 can also be used. The single connecting tube 62 would be affixed with stem 36, directly across from check valve 41, for attachment of air line 38, as indicated in FIG. 4 where the dotted outline represents airline 38 being directly connected to the single connecting tube 62. Embodiment 58 can be worn inside the upper portion of a brassiere of a female patient 44, with the bra providing the support, thus eliminating the need for strap 52. In some instances, just positioning the upper end of air line 38 within the central front section of the brazier provides enough support to prevent stress on tracheostomy tube 13.

Although specific structural details of the invention have been shown and described, it should be understood that changes and alterations may be practiced without departing from the spirit of the invention as defined in the claims.

What I claim as my invention is:

1. An apparatus for conserving oxygen during supplemental oxygen therapy on a human patient, said apparatus connectable between an oxygen supply source and an opening into a patient's respiratory system; said apparatus consisting essentially of:

at least one housing having a first chamber and a second chamber separated from one another by a diaphragm, said first chamber having a plurality of vent holes for preventing vacuum in the first chamber, said second chamber having at least one reservoir;

said at least one reservoir having at least one opening through which oxygen may pass, said diaphragm forming means for expanding and contracting said reservoir concomitantly with ingress and egress of oxygen into said reservoir;

conduit mans for establishing communication between said at least one opening, and an oxygen supply source and having an opening into a patient's respiratory system;

a one-way flow-direction check valve within said conduit means, said check valve further having means for closing upon exhalation by a patient for preventing air exhaled by a patient from entering said reservoir during therapy, said check valve further having means for opening upon inhalation by a patient for allowing withdrawal of oxygen from said reservoir by the patient during inhalation during therapy.

2. The apparatus of claim 1, wherein said opening to a patient's respiratory system further includes a tracheostomy tube assembly.

* * * * *